United States Patent [19]

Levy et al.

[11] 4,141,857

[45] Feb. 27, 1979

[54] SUPPORT MATRICES FOR IMMOBILIZED ENZYMES

[75] Inventors: Joseph Levy, Northbrook, Ill.; Murray C. Fusee, Ellicott City, Md.

[73] Assignee: UOP Inc., Des Plaines, Ill.

[21] Appl. No.: 842,993

[22] Filed: Oct. 17, 1977

Related U.S. Application Data

[63] Continuation-in-part of Ser. No. 681,987, Apr. 30, 1976, abandoned, which is a continuation-in-part of Ser. No. 550,898, Feb. 18, 1975, abandoned.

[51] Int. Cl.$^2$ ............................................. B01J 31/06
[52] U.S. Cl. .................................. 252/430; 252/428; 195/63; 195/68; 195/DIG. 11
[58] Field of Search ................... 195/63, 68, DIG. 11; 252/428, 430; 260/39 R, 395 B

[56] References Cited

U.S. PATENT DOCUMENTS

| | | | |
|---|---|---|---|
| 3,796,634 | 3/1974 | Haynes et al. | 195/63 |
| 3,821,083 | 6/1974 | Van Leemputten et al. | 195/63 |
| 3,941,718 | 3/1976 | Barabas et al. | 252/430 |
| 3,959,080 | 5/1976 | Orth et al. | 195/68 X |
| 3,980,583 | 9/1976 | Mitchell et al. | 252/430 |
| 4,003,848 | 1/1977 | Cotter et al. | 252/428 X |

*Primary Examiner*—Patrick Garvin
*Attorney, Agent, or Firm*—James R. Hoatson, Jr.; Raymond H. Nelson; William H. Page, II

[57] ABSTRACT

Support matrices for immobilized enzymes comprise a combined organic-inorganic support consisting of a porous inorganic support containing an organic polymeric material which possesses functionalized pendent groups, said polymeric material being entrapped and also adsorbed in part in the pores of the inorganic porous support. The organic polymeric component of the matrix constitutes a copolymer prepared in situ from a first polyfunctional monomer, a low molecular weight polymer, a low molecular weight polymer hydrolysate, or a preformed polymer of natural or synthetic origin which is reacted with an excess of a second bifunctional reactive monomer.

14 Claims, No Drawings

SUPPORT MATRICES FOR IMMOBILIZED ENZYMES

CROSS-REFERENCE TO RELATED APPLICATIONS

This application is a continuation-in-part of our copending application Ser. No. 681,987 filed Apr. 30, 1976, now abandoned which is a continuation-in-part of our copending application Ser. No. 550,898 filed Feb. 18, 1975, now abandoned all teachings of which are incorporated herein by reference thereto.

BACKGROUND OF THE INVENTION

It is known that enzymes, which are proteinaceous in nature and which are commonly water soluble, comprise biological catalysts which serve to regulate many and varied chemical reactions which occur in living organisms. The enzymes may also be isolated and used in analytical, medical and industrial applications. For example, they find use in industrial applications in the preparation of food products such as cheese or bread as well as being used in the preparation of alcoholic beverages. Some specific uses in industry may be found in the use of enzymes such as in the resolution of amino acids; in the modification of penicillin to form various substrates thereof; the use of various proteases in cheese making, meat tenderizing, detergent formulations, leather manufacture and as digestive aids; the use of carbohydrases in starch hydrolysis, sucrose inversion, glucose isomerization, etc.; the use of nucleases in flavor control; or the use of oxidases in oxidation prevention and in the color control of food products. These uses as well as many others have been well delineated in the literature.

As hereinbefore set forth, inasmuch as enzymes are commonly water soluble as well as being generally unstable and readily deactivated, they are also difficult either to remove from the solutions in which they are utilized for subsequent reuse or it is difficult to maintain their catalytic activity for a relatively extended period of time. The aforementioned difficulties will, of course, lead to an increase cost in the use of enzymes for commercial purposes due to the necessity for frequent replacement of the enzyme, this replacement being usually necessary with each application. To counteract the high cost of replacement, it has been suggested to immobilize or insolubilize the enzymes prior to the use thereof. By immobilizing the enzymes through various systems hereinafter set forth in greater detail, it is possible to stabilize the enzymes in a relative manner and, therefore, to permit the reuse of the enzyme which may otherwise undergo deactivation or be lost in the reaction medium. Such immobilized or insolubilized enzymes may be employed in various reactor systems such as in packed columns, stirred tank reactors, etc., depending upon the nature of the substrate which is utilized therein. In general, the immobilization of the enzymes provides a more favorable or broader environmental and structural stability, a minimum of effluent problems and materials handling as well as the possibility of upgrading the activity of the enzyme itself.

As hereinbefore set forth, several general methods, as well as many modifications thereof, have been described by which the immobilization of enzymes may be effected. One general method is to adsorb the enzyme at a solid surface as, for example, when an enzyme such as amino acid acylase is adsorbed on a cellulosic derivative such as DEAE-cellulose; papain or ribonuclease is adsorbed on porous glass; catalase is adsorbed on charcoal; trypsin is adsorbed on quartz glass or cellulose, chymotrypsin is adsorbed on kaolinite, etc. Another general method is to trap an enzyme in a gel lattice such as glucose oxidase, urease, papain, etc., being entrapped in a polyacrylamide gel; acetyl cholinesterase being entrapped in a starch gel or a silicone polymer; glutamic-pyruvic transaminase being entrapped in a polyamide or cellulose acetate gel, etc. A further general method is a cross-linking by means of bifunctional reagents and may be effected in combination with either of the aforementioned general methods of immobilization. When utilizing this method, bifunctional or polyfunctional reagents which may induce intermolecular cross-linking will covalently bind the enzymes to each other as well as on a solid support. This method may be exemplified by the use of glutaraldehyde or bisdiazobenzidine-2,2'-disulfonic acid to bind an enzyme such as papain on a solid support, etc. A still further method of immobilizing an enzyme comprises the method of a covalent binding in which enzymes such as glucoamylase, trypsin, papain, pronase, amylase, glucose oxidase, pepsin, rennin, fungal protease, lactase, etc., are immobilized by covalent attachment to a polymeric material which is attached by various means to an organic or inorganic solid porous support. This method may also be combined with the aforesaid immobilization procedures.

The above enumerated methods of immobilizing enzymes all possess some drawbacks which detract from their use in industrial processes. For example, when an enzyme is directly adsorbed on the surface of a support, the binding forces which result between the enzyme and the carrier support are often quite weak, although some prior art has indicated that relatively stable conjugates of this type have been obtained when the pore size of the support and the spin diameter of the enzyme are correlated. However, in such cases it is specified that the pore size of the support cannot exceed a diameter of about 1000 Angstroms. In view of this weak bond, the enzyme is often readily desorbed in the presence of solutions of the substrate being processed. In addition to this, the enzyme may be partially or extensively deactivated due to its lack of mobility or due to interaction between the support and the active site of the enzyme. Another process which may be employed is the entrapment of enzymes in gel lattices which can be effected by polymerizing an aqueous solution or emulsion containing the monomeric form of the polymer and the enzyme or by incorporating the enzyme into the preformed polymer by various techniques, often in the presence of a cross-linking agent. While this method of immobilizing enzymes has an advantage in that the reaction conditions utilized to effect the entrapment are usually mild so that often there is little alteration or deactivation of the enzyme, it also has disadvantages in that the conjugate has poor mechanical strength, which results in compacting when used in columns in continuous flow systems, with a concomitant plugging of the column. Such systems also have rather wide variations in pore size thus leading to some pore sizes which are large enough to permit the loss of enzyme. In addition, some pore sizes may be sufficiently small so that large diffusional barriers to the transport of the substrate and product will lead to reaction retardation, this being especially true when using a high molecular weight substrate. The disadvantages which are present when immobilizing an enzyme by intermolecular cross-linkage, as already noted, are due to the lack of mobility with resulting deactivation because of inability of the enzyme to assume the natural configuration necessary for maximum activity, particularly when the active site is involved in the binding process.

Covalent binding methods have found wide applications and may be used either as the sole immobilization technique or as an integral part of many of the methods already described in which cross-linking reactions are employed. This method is often used to bind the enzyme as well as the support through a bifunctional intermediary molecule in which the functional groups of the molecule, such as, for example, gamma-aminopropyltriethoxysilane, are capable of reacting with functional moieties present in both the enzyme and either an organic or inorganic porous support. A wide variety of reagents and supports has been employed in this manner and the method has the advantage of providing strong covalent bonds throughout the conjugate product as well as great activity in many cases. The covalent linkage of the enzyme to the carrier must be accomplished through functional groups on the enzyme which are non-essential for its catalytic activity such as free amino groups, carboxyl groups, hydroxyl groups, phenolic groups, sulfhydryl groups, etc. These functional groups will also react with a wide variety of other functional groups such as an aldehydo, isocyanato, acyl, diazo, azido, anhydro activated ester, etc., to produce covalent bonds. Nevertheless, this method also often has many disadvantages involving costly reactants and solvents, as well as specialized and costly porous supports and cumbersome multi-step procedures, which render the method of preparation uneconomical for commercial application.

The prior art is therefore replete with various methods for immobilizing enzymes which, however, in various ways fail to meet the requirements of economical industrial use. However, as will hereinafter be discussed in greater detail, none of the prior art compositions comprise the composition of matter of the present invention which constitutes an inorganic porous support containing a copolymer, formed in situ from a polyfunctional monomer, a low molecular weight polymer, a polymer hydrolysate, or a preformed polymer, of natural or synthetic origin by reaction with a bifunctional monomer, which is entrapped and also adsorbed in part within the pores of said support, and which contains terminally functionalized, pendent groups extending therefrom; the enzyme being covalently bound to the active moieties at the terminal reactive portions of the pendent groups, thus permitting the freedom of movement which will enable the enzyme to exercise maximum activity. A variable portion of the enzyme will also be adsorbed upon the matrix, but this will be recognized as an unavoidable consequence of almost all immobilization procedures involving porous inorganic supports and is not to be considered a crucial aspect of this invention. Furthermore, the bond between the inorganic support and the organic copolymer which has been prepared in situ in the pores of the support is not covalent but rather physico-chemical and mechanical in nature and the inorganic-organic matrix so produced presents high stability and resistance to disruption. As further examples of prior art, U.S. Pat. No. 3,556,945 relates to enzyme composites in which the enzyme is adsorbed directly to an inorganic carrier such as glass. U.S. Pat. No. 3,519,538 is concerned with enzyme composites in which the enzymes are chemically coupled by means of an intermediary silane coupling agent to an inorganic carrier. In similar fashion, U.S. Pat. No. 3,783,101 also utilizes an organosilane composite as a binding agent, the enzyme being covalently coupled to a glass carrier by means of an intermediate silane coupling agent, the silicon portion of the coupling agent being attached to the carrier while the organic portion of the coupling agent is coupled to the enzyme, the composition containing a metal oxide on the surface of the carrier disposed between the carrier and the silicon portion of the coupling agent. In U.S. Pat. No. 3,821,083 a water-insoluble polymer such as polyacrolein is deposited on an inorganic carrier and an enzyme is then covalently linked to the aldehyde groups of the polymer. However, according to most of the examples set forth in this patent, it is necessary to first hydrolyze the composite prior to the deposition of the enzyme on the polymer. Additionally the product which is obtained by the method of this patent suffers a number of disadvantages in that it first requires either the deposition, or initially the formation, of the desired polymer in an organic medium followed by its deposition on the inorganic carrier with a subsequent clean-up operation involving distillation to remove the organic medium. In addition to this, in another method set forth in this reference, an additional hydrolytic reaction is required in order to release the aldehyde groups from the initial acetal configuration in which they occurred in the polymer. Inasmuch as these aldehyde moieties are attached directly to the backbone of the polymer, the enzyme is also held adjacent to the surface of the polymer inasmuch as it is separated from the surface of the polymer by only one carbon atom of the reacting aldehyde group and, therefore, the enzyme is obviously subjected to the physico-chemical influences of the polymer as well as being relatively immobilized and inhibited from assuming its optimum configuration. Another prior art patent, namely, U.S. Pat. No. 3,705,084 discloses a macroporous enzyme reactor in which an enzyme is adsorbed on the polymeric surface of a macroporous reactor core and thereafter is cross-linked in place. By cross-linking the enzymes on the polymeric surface after adsorption thereof, the enzyme is further immobilized in part and cannot act freely as in its native state as a catalyst. The cross-linkage of enzymes in effect links them together, thereby preventing a free movement of the enzyme and decreases the mobility of the enzyme which is a necessary prerequisite for maximum activity.

U.S. Pat. No. 3,654,003 discloses a water-soluble enzyme conjugate which is prepared from an organic water-soluble support to which the enzyme is cross-linked and whose utility is limited only to cleaning compositions and pharmaceutical ointments. However, this enzyme composition also suffers from the disadvantages of the close proximity and interlocking of the enzyme and support, as well as the poor mechanical strength which is generally exhibited by enzyme conjugates based on organic polymeric supports.

U.S. Pat. No. 3,796,634 also discloses an immobilized biologically active enzyme which differs to a considerable degree from the immobilized enzyme conjugates of the present invention. The enzyme conjugate of this patent consists of an inorganic support comprising colloidal particles possessing a particle size of from 50 to 20,000 Angstroms with a polyethyleneimine, the latter being cross-linked with glutaraldehyde to staple the cross-linked polymer so formed as a monolayer on the surface of the colloidal particles, followed by adsorption of the enzyme directly onto this monolayer. Following this, the enzyme which is adsorbed as a monolayer on the surface of the colloidal particles is then cross-linked with additional glutaraldehyde to other adsorbed enzyme molecules to prevent them from being readily desorbed while in use. There is no indication of any covalent binding between enzyme and polymer matrix as is present in the present invention. By the enzyme molecules being cross-linked together on the surface of the support, this conjugate, therefore, is subjected to deactivation by both the cross-linking reaction and by the electronic and steric effects of the surface, said enzyme possessing limited mobility. Inasmuch as the product of this patent is colloidal in nature, it also possesses a very limited utility for scale-up to commercial operation, since it cannot be used in a continuous flow system such as a packed column because it would either be carried along and out of the system in the flowing liquid stream or, if a restraining membrane should be employed, the particles would soon become packed against the barrier to form an impervious layer. In addition, such a colloidal product could not readily be utilized in a fluidized bed apparatus, thereby limiting the chief utility to a batch type reactor such as a stirred tank type reactor from which it would have to be separated by centrifugation upon each use cycle. In contrast to this, the immobilized enzyme conjugates of the present invention may be employed in a wide variety of batch or continuous type reactors and therefore are much more versatile with regard to their modes of application.

In addition, another prior art reference U.S. Pat. No. 3,959,080 relates to a carrier matrix for immobilizing biochemical effective substances. However, the matrix which is produced according to this reference constitutes the product derived from the reaction of an organic polymer containing cross-linkable acid hydrazide or acid azide groups with a bifunctional cross-linking agent such as glutaraldehyde. However, this matrix also suffers from the relatively poor mechanical stability and other deficiencies which are characteristic of organic enzyme supports as well as the relatively complex organic reactions employed in preparing such polymeric hydrazides, etc.

This invention relates to novel compositions of matter comprising support matrices for immobilized enzymes. More specifically, the invention is concerned with support matrices consisting of a combined organic-inorganic composite in which the inorganic porous support material contains an organic copolymer which has been formed in situ from the reaction between a first polyfunctional monomer, a low molecular weight polymer, a low molecular weight polymer hydrolysate, or a preformed polymer of synthetic or natural origin with an excess of a second bifunctional monomer containing suitable reactive moieties. In addition, the invention is also concerned with a process for preparing these matrices. The organic copolymer material which forms one component of the support matrix is both entrapped and also adsorbed in part in the pores of the aforesaid porous support material, and is further provided with functionalized pendant groups extending therefrom, the functional moieties of said pendent group being located at the terminal portions thereof due to the use of a sufficient excess of the bifunctional monomer. This support material or matrix may be used as a support for immobilizing an enzyme which is covalently bound to the aforesaid functionalized pendant groups at the terminal reactive portions thereof.

As hereinbefore set forth, the use of enzymes in analytical, medical or industrial applications may be greatly enhanced if said enzymes are in an immobilized condition, that is, said enzymes, by being in combination with other solid materials, are themselves in such a condition whereby they are not water soluble and therefore they may be subjected to repeated use while maintaining the catalytic activity of said enzyme. In order to be present in an immobilized state, the enzymes must be bound in some manner to a water insoluble carrier, thereby being commercially usable in an aqueous insoluble state.

It is therefore an object of this invention to provide novel compositions of matter in which enzymes may be covalently bound in an immobilized state.

A further object of this invention is to provide a process for preparing combined inorganic-organic support matrices which are utilized for covalently binding an enzyme to the functionalized pendant groups at the reactive terminal portions thereof.

In one aspect an embodiment of this invention resides in a process for the preparation of a support matrix for enzymes which comprises treating an inorganic porous material possessing pore diameters of from about 100 to about 55,000 Angstroms and a surface area of from about 1 to about 500 square meters per gram with a solution of a first polyfunctional monomer, a low molecular weight polymer, a low molecular weight polymer hydrolysate or a preformed polymer; removing excess solution; contacting the treated porous material with a sufficient excess of a solution of a second bifunctional monomer to produce a resulting copolymer in situ containing terminally functionalized pendant groups; removing unreacted monomer solution; washing and recovering the resultant inorganic-organic support matrix.

A further embodiment of this invention is found in a support matrix for enzymes comprising an inorganic porous material which possesses pore diameters ranging from about 100 to about 55,000 Angstroms and a surface area of from about 1 to about 500 square meters per gram containing an organic copolymer material which possesses terminally functionalized pendant groups entrapped and also adsorbed in part in the pores of said inorganic porous material.

A specific embodiment of this invention resides in a process for the preparation of a support matrix for enzymes which comprises treating gamma-alumina with an aqueous solution of polyethyleneimine at a temperature in the range of from about 5° to about 60° C., removing unadsorbed polyethyleneimine, contacting the wet, treated gamma-alumina with an excess of an aqueous solution of glutaraldehyde at a temperature in the range of from about 5° to about 60° C. thereby forming a copolymer in situ which may also be cross-linked, removing unreacted glutaraldehyde and recovering the resultant inorganic-organic support matrix containing terminally functionalized pendant groups arising from the use of sufficient excess glutaraldehyde.

Another specific embodiment of this invention is found in a support matrix for enzymes comprising a porous silica-alumina-boron phosphate composite containing an organic polymeric material formed in situ in the pores of the composite by reacting polyethyleneimine adsorbed therein with an excess of glutaraldehyde, said polymeric material being entrapped and also adsorbed in part in the pores of said inorganic material.

Other objects and embodiments of this invention will be found in the following further detailed description of the present invention.

As hereinbefore set forth the present invention is concerned with support matrices for immobilized enzymes comprising a combined organic-inorganic material consisting of an inorganic porous support material of a type hereinafter set forth in greater detail containing a copolymeric organic material which is both entrapped and also adsorbed in part in the pores of said inorganic porous support. In addition, the copolymeric organic material will also contain pendant groups extending therefrom, said pendant groups containing terminally positioned functional moieties which will enable an enzyme to be covalently bound to said groups at the reactive terminal portions thereof. In contradistinction to other compositions of matter as set forth in the prior art, the support matrix of this invention may be prepared by utilizing relatively inexpensive reactants as well as utilizing more simple steps in the procedure for preparing said compositions. In addition, mechanical strength and stability of enzyme conjugates which result from the covalent binding of enzymes to the support matrices will be greater than that which is possessed by the immobilized enzymes of the prior art. Therefore, it is readily apparent that the compositions of matter of the present invention possesses economical advantages which are useful for industrial applications.

The compositions of matter of the present invention may be prepared in a relatively simple manner. In the preferred method of preparation, the inorganic porous support material will be treated with a solution, preferably aqueous in nature, of a polyfunctional monomer, a low molecular weight polymer, a polymer hydrolysate, or a preformed polymer, following which the unadsorbed solution is removed by any means known in the art such as draining, etc. It is also contemplated that other inexpensive organic solvents such as acetone, methanol, tetrahydrofuran, etc., may also be used as the carrier for the aforementioned initially added polyfunctional monomers or polymers. Following the removal of the unadsorbed solution, the wet porous support is then contacted with a sufficiently large excess of a second bifunctional monomer of from about 3 to about 50 or more mole proportions, relative to the initial additive which reacts therewith to provide pendant groups extending from the resulting copolymer containing unreacted terminal functional moieties. The reactive groups of the bifunctional monomer are preferably separated by a chain containing from about 4 to about 10 carbon atoms, which also may be a cyclic as well as a straight chain. This second bifunctional monomer will also be added preferably in an aqueous solution, whereby the copolymer which is both entrapped and also adsorbed in part in the pores of the inorganic support will be formed and from which pendant groups of the second monomer will extend. These pendant groups will contain unreacted terminal functional moieties due to the fact that a sufficient excess amount of the second bifunctional monomer was employed in treating the organic polymeric material originally adsorbed on the support. The unreacted functional moieties are then available for covalent binding to the enzyme, which is added to the resulting organic-inorganic matrix, again usually in an aqueous solution. After removal of the unreacted materials by conventional means such as by treating, washing, etc., the enzyme covalently bound to the pendant functionalized groups remains attached at the terminal portions thereof. It is therefore readily apparent that the entire immobilization procedure can be conducted in a simple and inexpensive manner, for example, in a column packed with the inorganic supports, utilizing an aqueous or inexpensive solvent media, the procedure being conducted over a temperature differential which may range from subambient (about 5° C.) up to elevated temperatures of about 60° C., and preferably at ambient (about 20°-25° C.) temperature, said procedure being effected by utilizing a minimum of operating steps and, in addition, permitting a ready recovery of the excess reactants, unbound enzyme and finished composition of matter, of which the former may be reused.

In describing the preparation of the organic-inorganic supports of this invention we wish it understood that the terms "first" and "second" reactants are employed to clearly represent the operating procedure but are not to be considered as limiting in nature. Thus the sequence of addition of those reactants may be reversed, if desired, particularly when the excess of the bifunctional monomer is in the lower part of the indicated range, although not necessarily with equivalent results.

Many of the inorganic supports reported in the prior art specify "controlled pore" materials such as glass, alumina, etc., having a pore diameter of from about 500 to 700 Angstroms for about 96% of the material and a maximum pore diameter of 1000 Angstroms, a surface area of about 40 to 70 m$^2$/gm and about 40–80 mesh size particles. In addition, these supports may be coated with metallic oxides such as zirconium oxide and titanium oxide for greater stability. In contradistinction to these supports, it is contemplated within the scope of this invention that the inorganic porous supports which are utilized herein, will constitute materials which possess pore diameters ranging from about 100 Angstroms up to about 55,000 Angstroms. The surface area of the particular inorganic porous support will also vary over a relatively wide range, said range being from about 1 to about 500 m$^2$/gm, the preferred range of surface area being from about 5 to about 400 m$^2$gm. The configuration of the inorganic porous support material will vary depending upon the particular type of support which is utilized. For example, the support material may be in spherical form, particulate form, as a ceramic monolith which may be coated with a porous inorganic oxide, etc., a membrane, ceramic fibers, alone or woven into a cloth, etc. The particle size may also vary over a wide range, again depending upon the particular type of support which is employed and also upon the substrate and the type of installation in which the enzyme conjugate is to be used. For example, if the support is in spherical form, the spheres may range in size from about 0.01" to about 0.25" in diameter, the preferred size ranging from about 1/32" to ⅛" in diameter. When the support is in particulate form, the particle size may also range between about the same limits. In terms of U.S. standard mesh sizes, such particles may range from about 2.5 to about 100 mesh, with about 10–40 mesh sizes preferred. Likewise, if the support is in the shape of ceramic fibers, the fibers may range from about 0.5 to about 20 microns in diameter or, if in the form of a membrane, the membrane may comprise a ceramic material which is cast into a thin sheet. It is to be understood that the aforementioned types of support configuration and size of the various supports are given merely for purposes of illustration, and it is not intended that the present invention be necessarily limited thereto.

It is also contemplated that the porous support materials may be coated with various oxides of the type hereinbefore set forth or may have incorporated therein various other inorganic materials such as boron phosphate, etc., these inorganic materials imparting special properties to the support material. A particularly useful form of support will constitute a ceramic body which may have the type of porosity herein described for materials of the present invention or it may be honeycombed with connecting macro size channels throughout, such materials being commonly known as monoliths, and which may be coated with various types of porous alumina, zirconia, etc. The use of such a type of support has the particular advantage of permitting the free flow of highly viscous substrates which are often encountered in commercial enzyme catalyzed reactions.

The inorganic porous support materials which are utilized as one component of the combined organic-inorganic matrix will include certain metal oxides such as alumina, and particularly gamma-alumina, silica, zirconia, silica-magnesia, silica-zirconia-alumina, etc., or gamma-alumina containing other inorganic compounds such as boron phosphate, etc., ceramic bodies, etc., as well as combinations of the aforementioned materials, one of said materials which may serve as a coating for another material comprising the support.

The copolymeric materials which are formed in situ in such a manner so that the copolymeric material is both entrapped and also adsorbed in part in the pores of the inorganic support of the type hereinbefore set forth may be produced according to the general methods hereinbefore described, that is, by first adsorbing a solution containing from about 2 to about 50% of a polyfunctional monomer, polymer hydrolysate, or a preformed polymer, including low molecular weight forms thereof; these polymeric additives being synthetic or naturally occurring in origin, and which are preferably soluble in water or other solvents which are inert to the reactions subsequently employed. As hereinbefore set forth, it is contemplated within the scope of this invention that a second bifunctional monomer is then added in similar manner in solution to form an organic-inorganic matrix by further reaction with the original polyfunctional additive adsorbed on the inorganic support to produce a copolymer which may also be crosslinked. As hereinbefore set forth the second bifunctional monomer reactant is present in an excess as needed to produce pendant terminally functionalized groups in the range of from about 2 to about 50 moles or more of bifunctional monomer per mole of monomer, hydrolyzed polymer or preformed polymer adsorbed on the inorganic support. The amount of the first monomer, etc., which is adsorbed on the support will depend on many variables including the type of porous support, the pH of the solution in which it is dissolved, the concentration of the material which is present, as well as reaction parameters including temperature, pressure, etc. While the excess of the second bifunctional monomer may range from about 2 to about 50 moles or more per mole of the original additive, etc., it is usually satisfactory that the excess be in the range of from about 4 to about 25 moles of bifunctional monomer. The unreacted excess monomer may be readily recovered for reuse as well as the unadsorbed polymeric material originally added to the support.

The functional groups which are present on the bifunctional monomer will comprise well-known reactive moieties such as amino, hydroxyl, carboxyl, thiol, carbonyl, etc., moieties. As was also hereinbefore set forth, the reactive groups of the bifunctional compounds are preferably, but not necessarily, separated by chains containing from about 4 to about 10 carbon atoms. The reactive moieties are capable of covalently bonding with both the initial additives and subsequently, after washing out unreacted materials, with the enzyme which is to be added in a subsequent step, said enzyme being then covalently bound to the functional group at the terminal portion of the pendant chain. After addition of the enzyme to this composition, a relatively stable enzyme conjugate will be produced which possesses high activity and high stability. The unadsorbed enzyme can also be recovered for reuse.

Specific examples of polyfunctional monomers, low molecular weight polymers, polymer hydrolysates or preformed polymers which may be initially adsorbed on the inorganic support will include water soluble polyamines such as ethylenediamine, diethylenetriamine, triethylenetetramine, tetraethylenepentamine, pentaethylenehexamine, hexamethylenediamine, polyethyleneimine, etc.; water insoluble but solvent or aqueous acid soluble polyamines such as methylenedicyclohexylamine, methylenedianiline, etc., and natural and synthetic, partially hydrolyzed polymers and preformed polymers, soluble in either aqueous or solvent media, such as partially hydrolyzed Nylon, collagen, polyacrolein, polymaleic anhydride, alginic acid, casein hydrolysate, gelatin, etc. Some specific examples of intermediate bifunctional monomeric materials which may be added to the above enumerated products in an excess in the range hereinbefore set forth to produce an organic-inorganic matrix and which possess the necessary characteristics hereinbefore set forth include compounds such as glutaraldehyde, adipoyl chloride, sebacoyl chloride, toluenediisocyanate, hexamethylenediisocyanate, terephthalic diesters or acyl halides, etc. Due to the large excess of intermediary, or spacer, bifunctional monomeric molecules which are used, the polymeric matrix which is formed will contain pendant groups comprising the spacer molecules, said molecules extending from the matrix and having reactive moieties available at the terminal portions thereof which are capable of reacting with the binding the enzyme to the spacer molecules via covalent bonds. Therefore, it is readily apparent that a suitable organic-inorganic matrix which is applicable in many situations will be formed with the support material by adsorbing any of the type of materials hereinbefore described which are known to the art and then treated with any bifunctional monomer molecule which is also known to the art and is suitably functionalized to react with the original additive, provided that a large enough excess of the bifunctional molecule is used to provide pendant groups which are capable of subsequently reacting with the enzyme which is desired to be immobilized. By utilizing these functional pendant groups as a binding site for the enzymes, it will permit the enzymes to have a greater mobility and thus permit the catalytic activity of the enzyme to remain at a high level for a relatively longer period of time than will be attained when the enzyme has been immobilized by any of the other methods such as entrapment in a gel lattice, adsorption on a solid surface or crosslinkage of the enzyme with adjacent enzyme molecules by means of bifunctional reagents, etc. Not all formulations, however, will produce equivalent results in terms of stability or activity.

Examples of enzymes which may be immobilized by a covalent bonding reaction and which contain an amino group capable of reacting with an aldehydic, isocyanato, acyl, ester, etc., moiety of the pendent group which is attached to a polymeric material entrapped and also adsorbed in part in the pores of a porous support material will include trypsin, papain, hexokinase, beta-galactosidase (lactase), ficin, bromelain, lactate dehydrogenase, glucoamylase, chymotrypsin, pronase, glucose isomerase, acylase, invertase, amylase, glucose oxidase, pepsin, rennin, protease, xylanase, cellulase, etc. In general any enzyme whose active site is not involved in the covalent bonding can be used although not necessarily with equivalent results. While the aforementioned discussion was centered about pendant groups which contain as a functional moiety thereon an aldehydic or isocyanato group, it is also contemplated within the scope of this invention that the pendent group can contain other functional moieties capable of reaction with carboxyl, sulfhydryl or other moieties usually present in enzymes. However, the covalent bonding of enzymes containing these other moieties with other pendant groups may not necessarily be effected with equivalent results and may also involve appreciably greater costs in preparing intermediates. It is to be understood that the aforementioned listing of porous solid supports, monomers, hydrolysates, polymers and enzymes are only representative of the various classes of compounds which may be used, and that the present invention is not necessarily limited thereto.

The preparation of the compositions of matter of the present invention is preferably effected in a batch type operation as heretofore already described in detail, although it is also contemplated within the scope of this invention that the formation of the finished composition of matter may also be effected in a continuous manner of operation. When a continuous type operation is used, a quantity of the porous solid support material is placed in an appropriate apparatus, usually constituting a column. The porous solid support material may be in any form desired such as powder, pellets, monoliths, etc., and is charged to the column, after which a preferably aqueous solution of, for example, a polyfunctional amine is contacted with the porous support until the latter is saturated with the amine solution and the excess is then drained. An intermediary spacer such as a reactive bifunctional monomer molecule such as glutaraldehyde is then contacted with the saturated support, said bifunctional molecule being present in an excess in the range of from about 2 to about 50 moles or more per mole of polyfunctional amine, as hereinbefore set forth. The formation of the copolymeric matrix is thus effected in an aqueous system, said reaction being effected during a period of time which may range from about 1 to about 10 hours or more in duration, but is usually of short duration. Following the completion of the desired residence time the excess glutaraldehyde is removed by draining and washing out any water soluble and unreacted materials, which in the case of a polyamine is preferably done with a buffer solution possessing a pH of about 4.

To form an immobilized enzyme conjugate an aqueous solution of an enzyme of the type hereinbefore set forth in greater detail is contacted or recycled through the column thereby effecting a covalent bonding of the enzyme to the terminal aldehydric groups of the functionalized pendant moieties which extend from the matrix. This occurs until there is no further covalent binding of the enzyme to the pendant molecules. The excess enzyme is recovered in the effluent after draining and washing the column, the column thus being ready for use in chemical reactions in which the catalytic effect of the enzyme is to take place. These procedures are, for the most part, conducted within the time, temperature and concentration parameters hereinbefore described in the batch type procedure and will result in comparable immobilized enzyme complexes. It is also contemplated within the scope of this invention that with suitable modifications of pH and temperature parameters which will be obvious to those skilled in the art, the process may be applied to a wide variety of inorganic porous supports, polymer forming reactants and enzymes.

The following examples are given for purposes of illustration of the novel compositions of matter of the present invention and to methods for preparing the same. However, these examples are given merely for purposes of illustration and it is to be understood that the present invention is not necessarily limited thereto.

EXAMPLE I

In this example 2 grams of a porous silica-alumina composite which contained boron phosphate incorporated therein having a particle size of 40–80 mesh, a pore diameter ranging from about 100 to about 55,000 Angstroms, and a surface area of about 150–200 $m^2/gm$ was utilized as the inorganic support for the novel composition of matter of the present invention. This support was calcined at a temperature of about 500° F. to remove any adsorbed moisture contained therein. Thereafter the support was treated with 25 ml of a 4% aqueous solution of tetraethylenepentamine (hereinafter denoted as TEP) at ambient temperature for a period of 1 hour in vacuo to facilitate the penetration of the solution into the pores of the support. The excess unabsorbed solution was then decanted, about 25% of the tetraethylenepentamine having been absorbed into the pores of the support. Following this, the wet support was then treated with 25 ml of a 5% aqueous solution of glutaraldehyde at ambient temperature and an almost immediate reaction took place with the formation of an insoluble reaction product both on the surface and within the pores of the support. These excess glutaraldehyde solution was then decanted and the organic-inorganic complex was washed to remove unreacted and unadsorbed reagents, said washing being accomplished first with water followed by washing with a 0.02 molar acetate buffer solution which possessed a pH of 4.2, the washing operation being effected at a temperature of 45° C. Thereafter an enzyme solution containing about 200 mg. of glucoamylase per 25 ml of water was added and allowed to react with the composite at ambient temperature for a period of 1 hour. At the end of this 1-hour period, the excess glucoamylase solution was decanted and the enzyme conjugate was washed with water to remove any unbound and/or unadsorbed enzyme. The composition was then leached for a period of 24 hours with an acetate buffer solution similar to that hereinbefore described. Analysis of the product by micro Dumas gas chromatography both before and after addition of the enzyme showed that enzyme had been bound to the matrix and subsequent treatment with aqueous 30% thinned starch demonstrated that an active immobilized glucoamylase conjugate had been formed which was capable of hydrolyzing starch to glucose. It was also noted that the conjugate was quite stable having suffered only relatively minor losses during the leaching operation with the pH 4.2 buffer solution. This was demonstrated by finding little enzyme activity in the effluent from this leaching treatment.

Also, it is to be further noted that the availability of excess bifunctional monomer such as glutaraldehyde in the reaction with TEP becomes quite apparent inasmuch as 75% or more of the offered TEP is drained away from the inorganic support prior to addition of the aldehyde and that, subsequently, any unreacted glutaraldehyde is also washed out of the matrix before the addition of the enzyme.

EXAMPLE II

In this example, 2 grams of porous alumina spheres of about 20-25 mesh size, having a surface area of about 16 $m^2$/gm, and ABD of about 0.79 and a macropore size distribution of from about 100 to 58000 A°, of which about 81% of the pores were in the range of about 1000 to 1750 A° in diameter, were contacted with 8 ml of a 5% aqueous polyethyleneimine (PEI-18, Dow Chem. Co.) solution for one hour at ambient temperature. The unadsorbed PEI solution was then decanted and the alumina support containing the adsorbed PEI was subjected to treatment with excess glutaraldehyde, employing 6 ml of a 25% aqueous solution of the aldehyde, at ambient temperature for about one hour with occasional agitation. A co-polymer of PEI and glutaraldehyde was thereby produced forming an inorganic-organic matrix with the alumina support and containing pendant hydrocarbon groups terminally functionalized with aldehyde moieties arising from the use of excess glutaraldehyde. This reactive matrix was then washed free of unreacted glutaraldehyde and loosely held co-polymer fragments with water, after which it was treated with 192 units of the enzyme, glucoamylase, in 2 ml water and the immobilization allowed to proceed overnight at about 4° C. The resulting immobilized glucoamylase conjugate, in which the enzyme was covalently bound to the free aldehyde functions of the heretofore described pendant groups, was then washed thoroughly with 2M aqueous sodium chloride solution to remove any adsorbed enzyme. It was subsequently packed into a suitable column and assayed at 60° C. under continuous flow conditions by passing a 30% aqueous thinned starch solution through the conjugate bed and determining the glucose content of effluent samples by conventional procedures. One unit of glucoamylase activity refers to the amount of enzyme which is capable of producing 1 gram glucose per hour at 60° C. and pH = 4.2 from a 30% thinned, aqueous starch solution and corresponds to about 92.6 international units of activity which is defined as the amount of enzyme which will produce 1 micromole of glucose per min. under these conditions. The immobilized conjugate was found to have an activity of 3.5 units, as previously defined, or 324 international units per gram.

EXAMPLE III

In this example 2 gm of calcined 10-30 mesh porous silica-alumina composite which contained boron-phosphate was treated with 25 ml of 4% tetraethylenepentamine (TEP) at ambient temperature for about one hour under vacuum. After this time the unadsorbed TEP solution was decanted and to the still moist TEP treated alumina support was added 25 ml of 25% glutaraldehyde. The glutaraldehyde was allowed to react for about one hour with occasional swirling also at ambient temperature and after this time, the unreacted glutaraldehyde solution was decanted and the inorganic-copolymer matrix so formed was washed three times with 25 ml of 0.02 sodium acetate buffer solution. The glucoamylase enzyme solution (25 ml of a 2:25 ratio of Diazyme L-100: water) was added, and allowed to react for one hour with occasional swirling. The unreacted enzyme solution was decanted and the enzyme conjugate washed three times with 0.02M sodium acetate buffer. The conjugate was further leached with fresh 0.02M buffer overnight to insure removal of adsorbed enzyme. The immobilized conjugate yielded 6.5 units (600 international units)/gram conjugate when batch assayed against 30% weight by volume thinned starch by the Worthington glucostat analysis for glucose.

EXAMPLE IV

An organic-inorganic matrix containing free aldehyde moieties was prepared in a manner similar to that of example I except that 50% aqueous glutaraldehyde was employed instead of 25%, and the porous alumina particles had a macropore size distribution ranging mostly from about 500-1750 A° in diameter, an ABD of 0.83 and a surface area of about 11 $m^2$/gram. To 1 gram of this activated matrix was added 180 units of glucose isomerase in 1 ml aqueous solution and immobilization allowed to take place overnight at a temperature of about 4° C. The conjugate was then washed free of unbound enzyme with water, the effluent containing 12 units of activity, after which further washing with 2M aqueous sodium chloride solution was employed to remove any adsorbed enzyme. The conjugate was then placed in a suitable column and assayed for activity by the continuous flow technique with 45% aqueous fructose solution. The immobilized enzyme showed an activity of 101.5 units per gram with a coupling efficiency of 60.4%. In this case one international unit of GI activity is defined as the amount of enzyme which will produce one micro mole of glucose per min at 60° C. from a 45% aqueous fructose solution of pH 7.5.

EXAMPLE V

In a manner similar to that set forth in Example I above, 2 grams of a silica-alumina composite possessing the same physical characteristics of particle size, pore diameter and surface area as that set forth in Example I may be treated with a tetrahydrofuran solution of tetraethylenepentamine (TEP) and followed by a toluenediisocyanate solution also in tetrahydrofuran instead of aqueous glutaraldehyde. After decanting the excess diisocyanate solution and washing with tetrahydrofuran, the organic-inorganic complex may then be further treated with an aqueous glucoamylase solution. As in Example I, the finished product will comprise an active, completely immobilized enzyme complex.

EXAMPLE VI

To illustrate the point that various concentrations of solutions can be used to prepare the desired product, the procedure set forth in Example I above was repeated with the exception that more highly concentrated solutions of the various reagents were used. For example, 2 grams of a 10-30 mesh, porous silica-alumina composite was treated with 25 ml of a 20% tetraethylenepentamine (TEP) solution and after decanting, 50 ml of a 25% glutaraldehyde solution was added thereto. This complex, after washing, was then treated with aqueous glucoamylase to prepare an active immobilized enzyme conjugate.

EXAMPLE VII

In this example a silica-alumina composite having a particle size of 10-30 mesh, a pore diameter ranging from about 100 to about 55,000 Angstroms and a surface area of from about 150-200 m$^2$/gm is treated by adding 25 ml of a pentaethylenehexamine solution. After draining and reacting with glutaraldehyde, the organic-inorganic matrix is then treated with a glucoamylase solution according to the general procedure of Example I to prepare an active enzyme conjugate.

EXAMPLE VIII

In this example a column possessing an inside diameter of 20 mm contained 14.2 grams of an active enzyme conjugate prepared from glucoamylase which was bonded to a 10-30 mesh silica-alumina porous support containing boron phosphate incorporated therein, the conjugate having been prepared in a manner similar to that set forth in Example I above. The column was used continuously for a period of 30 days at a temperature of 45° C. to hydrolyze an aqueous 30% thinned starch solution which had been buffered to a pH of 4.2. The effluent was monitored for the glucose production using a Worthington glucostat procedure. It was found that there was apparently only a relatively slow decrease in enzyme activity during this period of time and that the percentage of conversion of starch to glucose at this temperature and at a flow rate of about 150 ml per hour was 62%.

EXAMPLE IX

To illustrate the fact that various substrates or supports may be utilized to prepare the desired compositions of matter, an alumina coated monolith which consisted of a ceramic body honeycombed with connecting macro size channels was treated in a manner similar to that set forth in Example I above, that is, the monolith was treated with solutions of tetraethylenepentamie, (TEP) glutaraldehyde and a glucoamylase enzyme, the treatment being carried out in a sequential operation which included decanting, washing, and leaching procedures hereinbefore described. The original ceramic monolith possessed a dry weight of 256 grams, of which 13% consisted of an alumina coating. The finished immobilized enzyme conjugate was elaborated into a column within a glass tube having an inside diameter of 70 mm in order that it could be operated continuously by means of a suitable pumping apparatus within a temperature controlled container, said container being maintained at a temperature of 45° C. Over a 40-day period of continuous usage for the hydrolysis of a 30% buffered thinned starch solution, it was found that there was a relatively small loss of the original activity of the enzyme conjugate while maintaining a flow rate of about 85 ml per hour. In addition, it was found that during the 40-day period, there was an approximate 80% conversion of the starch to glucose. In order to further study the properties of the system, subsequent variations in flow rate were made during which it was found that at a flow rate of about 38 ml per hour it was possible to obtain a conversion in the range of from 92-93% of starch to glucose. The relatively long period of time during which this enzyme was used to convert starch to glucose without a significant loss of enzyme activity either by desorption or deactivation indicated a long half life of the catalyst.

EXAMPLE X

In this example a monolith type of conjugate and column similar to that described in Example VIII above was prepared, the exception being that the enzyme which was used to prepare the complex comprised lactase in place of glucoamylase. The conjugate was tested for stability under a continuous flow while maintaining the temperature at 37° C. for a period of 29 days. It was again found that there was relatively little apparent loss of activity of the immobilized enzyme conjugate. This immobilized enzyme was used in the treatment of a 5% lactose solution which had been buffered to a pH of 4.2, said lactose solution being charged to the column at a rate of 54 ml per hour. It was found during the 29-day period that there was about a 35% conversion of lactose to glucose and galactose.

EXAMPLE XI

To illustrate the presence of an excess of the bifunctional monomer, a binding procedure was effected utilizing 2.7 grams of a silica-alumina containing boron phosphate and which possessed a pore size ranging from 100 to 55,000 Angstroms. The particulates which were from 10-30 mesh in size were treated with 25 cc of a 2% TEP solution and after draining, the treated particulates then were treated with 25 cc of a 25% solution of glutaraldehyde. The organic-inorganic matrix thus formed was then washed free of unreacted reagents and dried in vacuum. Following this, the amount of contained organic polymer was analyzed for nitrogen and carbon content. The analysis indicated 1.53% nitrogen and 13.7% carbon, from which data it was calculated that the ratio of glutaraldehyde to TEP was about 8.2 moles per one mole. Therefore the organic polymeric material of necessity contained pendant groups extending therefrom with terminal aldehydic moieties to which an enzyme could be covalently bonded. In addition, a similarly prepared TEP-glutaraldehyde reaction product using a 4% TEP solution and a 5% glutaraldehyde solution showed, upon examination by infrared analysis, the presence of carbonyl groups.

EXAMPLE XII

To illustrate the fact that immobilized enzyme conjugates of the present invention could be utilized in a continuous manner, as opposed to enzyme conjugates of the prior art which, due to their particular configuration, could not be used in continuous operations, two experiments were performed. In one experiment 22 grams of a silica-alumina coated monolith containing interconnecting macro size channels was placed in a column type apparatus suitable for continuous flow operation. In this column, the monolith was treated with glucoamylase by simple adsorption. In a second column 22 grams of the monolith was submitted to the immobilization procedure of the present invention, that is, by treatment with TEP followed by treatment with an excess of glutaraldehyde and the addition of glucoamylase to the organic-inorganic matrix. In the first column hydrolysis of a 30% thinned starch solution at 45° C. and at a residence time of 2.38 hours afforded a 25% conversion of glucose and a half life of about 30 days. In contradistinction to this, the second column which contained the immobilized enzyme conjugate of the present invention afforded a conversion of about 38% at 45° C. and at a residence time of 2.7 hours with virtually no loss of activity after a period of 41 days of continuous operation.

EXAMPLE XIII

To illustrate the necessity for the presence of a copolymer produced from the reaction of a polyfunctional monomer, a low molecular weight polymer, a hydrolyzed polymer or a preformed polymer with a bifunctional monomer of the type hereinbefore set forth, a conjugate was prepared utilizing a silica-alumina similar to that set forth in the above examples. However, in one instance the inorganic porous support was treated with 4% TEP followed by addition of glucoamylase omitting the intermediate addition of glutaraldehyde. This conjugate was utilized as a catalyst for the conversion of a 30% starch solution and was found to possess an activity of only 0.3 units per gram. In a similar manner when the inorganic porous support was treated with only a 5% glutaraldehyde solution followed by addition of glucoamylase the activity of the conjugate to convert starch to glucose was only 1.0. This therefore indicates that neither of these reagents by themselves serves to effectively immobilize an enzyme to an inorganic support.

EXAMPLE XIV

To illustrate the effectiveness and high activity of an immobilized enzyme conjugate in which lactase comprised the enzyme, a series of experiments was performed in which the inorganic porous supports possessed different configurations. In the first experiment ⅛" alumina spheres in which 51% of the pore size ranged between 500 and 1000 Angstroms and 27% between 300 and 500 Angstroms, an apparent bulk density of about 0.3 and a surface area of 184 m$^2$/gm was treated with 25 cc of a 2% TEP solution. The pH of the solution was adjusted to 3.5, the excess was drained and 25 cc of a 6.6% glutaraldehyde solution was added. The resulting organic-inorganic matrix was washed and 1000 milligrams of lactase dissolved in 25 cc of water was added. The resulting immobilized enzyme conjugate was washed and utilized as a catalyst. The conjugate had a batch activity of 152.7 units per gram and a coupling efficiency of about 14%.

When a particulate of the above described support having a size of from 40–80 mesh was subjected to a binding procedure in which 25 cc of a 6% TEP solution adjusted to a pH of 3.5 was added, the excess drained and 39.7 cc of a 25% glutaraldehyde solution was then added followed by washing and the addition of 250 milligrams of lactase in 25 cc of water was assayed, it was found that the conjugate had a batch activity of 328.1 units per gram with a coupling efficiency of 62.1%; one unit of activity representing the production of one micromole of glucose produced per minute at 40° from 20% lactose at pH=4.2 during a 0.5 hr. assay period.

In this experiment silica-alumina spheres having a diameter of 1/16" and which possessed a pore size in which 43.6% ranged between 500 and 1000 Angstroms and 18.1% between 1000 and 1750 Angstroms was converted to an inorganic-organic matrix with 25 cc of a 2% TEP solution followed by 25 cc of a 6.6% glutaraldehyde solution, washed and then treated with 100 cc of lactase in 25 cc of water. The resulting conjugate had a batch activity of about 218 units per gram and a coupling efficiency of 60.0%.

In this experiment dense gamma-alumina spheres which were prepared in a marumerizing operation in which 86% of the pore size ranged from 1000 to 1750 Angstroms and which had a surface area of only 9.0 m$^2$/gm was first treated with 8 cc of a 6.25% TEP solution; the excess was drained and 25 cc of 13.2% glutaraldehyde was added to produce the matrix following which the latter was washed and 250 milligrams of lactase in 10 cc of water was added to covalently bind the enzyme to the matrix. An assay of the enzyme conjugate disclosed that it had a batch activity of 195.6 units per gram and a coupling efficiency of 42.2%. A similar immobilized enzyme conjugate prepared from alumina spheres having a surface area of 19 m$^2$/gm in which 68% of the pore size ranged from 1000 to 1750 Angstroms which was treated successively with 8 cc of a 2.5% TEP solution, 25 cc of a 25% glutaraldehyde solution and 200 milligrams of a lactase preparation sold commercially as Wallerstein's Lactase-LP consisting of about 10% enzyme and 90% sucrose dissolved in 10 cc of water possessed a batch activity of 409 units per gram and a coupling efficiency of 75.8%.

EXAMPLE XV

To illustrate the effect of an excess of bifunctional monomer over the initial additive, a series of immobilized lactase enzyme conjugates was prepared from ⅛" alumina spheres using various molar ratios of glutaraldehyde to TEP. The various enzyme conjugates were prepared in a manner similar to that set forth in the above examples using equal (25 cc) volume of TEP and glutaraldehyde. The results of these experiments are set forth in Table I below:

TABLE I

| % TEP | % Glutar. | Molar Ratio Glutar:TEP Offered | pH of TEP Soln. | Batch Activity Units/gm |
|---|---|---|---|---|
| 2.0 | 1.32 | 1.25 | 3.5 | 77.5 |
| 2.0 | 6.6 | 6.25 | 3.5 | 138.4 |
| 2.0 | 25.0 | 23.6 | 3.5 | 184.9 |
| 6.0 | 3.96 | 1.25 | 3.5 | 140.5 |
| 6.0 | 18.92 | 6.25 | 3.5 | 190.9 |

In addition, another series of experiments was performed to illustrate that the pH at which the enzyme is covalently bound to the organic-inorganic matrix may vary over a relatively wide range of from 3 to 11 or more. As in the previous experiments ⅛" diameter alumina spheres were treated with 25 cc of a TEP solution and 25 cc of a glutaraldehyde solution to form the organic-inorganic matrix. As in the previous binding procedures, the solid porous support containing the TEP was washed and drained prior to the addition of the glutaraldehyde solution. The organic-inorganic matrix was washed, drained and treated with 500 milligrams of a lactase preparation described in Example XIV above per gram of support. The addition of the TEP solution was, as hereinbefore set forth, effected at varying pH's. The effect of the pH on the activity of the bound lactase is set forth in Table II below:

TABLE II

| pH of TEP Solution | % TEP | % Glutar. | Batch Activity |
|---|---|---|---|
| 11.3 | 2.0 | 6.6 | 101.4 |
| 6.0 | 2.0 | 6.6 | 131.2 |
| 4.5 | 2.0 | 6.6 | 138.4 |
| 3.0 | 2.0 | 6.6 | 152.7 |
| 11.3 | 6.0 | 19.82 | 77.5 |
| 6.0 | 6.0 | 19.82 | 122.3 |

TABLE II-continued

| pH of TEP Solution | % TEP | % Glutar. | Batch Activity |
|---|---|---|---|
| 3.5 | 6.0 | 19.82 | 190.9 |

EXAMPLE XVI

To demonstrate that only a small portion of the TEP which is offered is adsorbed on the solid supports after treatment of said support with a TEP solution followed by draining, thereby creating even higher molar ratios of glutaraldehyde to TEP under reaction conditions that would be calculated from the ratios of materials offered, 2 grams of ⅛" alumina spheres were treated with 25 cc solutions of TEP in which the TEP was present in a range of from about 1% to about 50% of the solution. In the first series of experiments, 4 samples of the alumina spheres were treated with TEP solutions ranging from 4% to 50% at a pH of about 11.5. After draining the support it was subjected to analysis with the following results:

TABLE III

| % TEP Offered | Gms TEP Offered | Gms TEP Adsorbed | % TEP Adsorbed |
|---|---|---|---|
| 4.0 | 1.0 | 0.069 | 6.9 |
| 8.0 | 2.0 | 0.109 | 5.5 |
| 16.0 | 4.0 | 0.234 | 5.0 |
| 50.0 | 12.5 | 0.666 | 5.3 |

When the experiments were repeated by treating the support with four solutions varying from 1% to 12% and adjusting the pH to about 4.0 by the addition of hydrochloric acid the supports, after draining off the solution, were analyzed with the following results:

TABLE IV

| % TEP Offered | Gms TEP Offered | Gms TEP Adsorbed | % TEP Adsorbed |
|---|---|---|---|
| 1.0 | 0.25 | 0.0146 | 5.84 |
| 2.0 | 0.50 | 0.0168 | 3.36 |
| 6.0 | 1.50 | 0.0984 | 6.56 |
| 12.0 | 3.00 | 0.1742 | 5.81 |

EXAMPLE XVII

In this example a column was packed with alumina spheres prepared according to the marumerizing procedure. These spheres were then treated in a manner similar to that set forth above by the addition of a TEP solution followed by draining and the addition of an excess of glutaraldehyde solution. The immobilized enzyme conjugate was completed by treating the resulting organic-inorganic matrix with lactase. Thereafter the immobilized enzyme conjugate was used as a catalyst for both a lactose solution and a whey permeate. The plant was run at a temperature of 40° C. for a period of 620 hours using a space velocity of about 5.0. The results are set forth in Table V below:

TABLE V

| Total Hrs. On Stream Lactose Feed Followed by Whey | Hrs. Life Study (Whey Feed) | Glucose Prod (mg/ml) | % Conversion |
|---|---|---|---|
| 241.0 | 0.0 | 17.3 | 65.8 |
| 257.5 | 16.5 | 17.65 | 67.1 |
| 280.2 | 39.2 | 17.75 | 67.5 |
| 287.0 | 46.0 | 17.0 | 64.6 |
| 304.2 | 63.2 | 17.15 | 65.2 |
| 312.8 | 71.2 | 17.15 | 65.2 |
| 329.0 | 88.0 | 16.0 | 60.8 |
| 335.8 | 94.8 | 16.45 | 62.5 |

TABLE V-continued

| Total Hrs. On Stream Lactose Feed Followed by Whey | Hrs. Life Study (Whey Feed) | Glucose Prod (mg/ml) | % Conversion |
|---|---|---|---|
| 424.2 | 183.2 | 16.7 | 63.5 |
| 432.2 | 191.2 | 17.05 | 64.8 |
| 448.2 | 207.2 | 17.0 | 64.6 |
| 454.2 | 211.2 | 17.15 | 65.2 |
| 456.2 | 215.2 | 17.50 | 66.5 |
| 570.0 | 329.0 | 16.1 | 61.2 |
| 574.0 | 333.0 | 15.25 | 58.0 |
| 592.2 | 351.2 | 17.65 | 67.1 |
| 598.0 | 357.0 | 17.3 | 65.8 |
| 601.0 | 360.0 | 17.5 | 66.2 |
| 615.5 | 374.5 | 17.05 | 64.8 |
| 620.2 | 379.2 | 17.1 | 65.0 |

It is therefore readily apparent that the immobilized enzyme conjugate of the present invention maintained a relatively steady activity in the percent conversion of the lactose-whey permeate feed to glucose and galactose during the 620 hour period of the test.

In contradistinction to this, when lactase was adsorbed on the marumerized spheres without first preparing an organic polymer as a component of the matrix, the conversion to glucose plus galactose dropped from 100% at the beginning to about 28% at the end of 450 hours.

EXAMPLE XVIII

In this example, an additional series of experiments were performed in which porous alumina spheres of about 12/20 mesh particle size, which possessed an apparent bulk density (ABD) of 0.93, a surface area of about 7 m²/gm, and a pore size distribution in which about 97% were in a range of from about 300 to 1750 Angstroms were contacted with a 6.25% aqueous TEP solution for a period of about 1 hour at a temperature of about 25° C. with intermittent shaking. At the end of this time, the unadsorbed TEP was decanted and the treated support was rinsed with distilled water. The alumina spheres containing the adsorbed TEP were then treated with varying amounts of 25% aqueous glutaraldehyde at room temperature for a period of about 1 hour while occasionally shaking the mixture. Thereafter the unreacted glutaraldehyde was washed out with water and the enzyme comprising an aqueous lactase solution was added. The so treated spheres were allowed to stand for about 3 hours at room temperature in contact with the enzyme solution and then washed with water and a buffer solution of pH=4.2 to remove unbound enzyme. In these experiments, the molar ratio of glutaraldehyde to adsorbed TEP varied from 0 to 10. The different immobilized enzyme conjugates were then packed into individual columns which were operated in a continuous manner for a period of 41 days employing a substrate solution consisting of a 5% aqueous lactose solution which contained 0.5% NaCl. At the conclusion of the tests, the residual activity of the enzyme conjugates were measured with the results set forth in Table VI below:

TABLE VI

| Molar Ratio Glutaraldehyde/Adsorbed TEP | Residual Activity % |
|---|---|
| 10 | 42 |
| 1 | 31 |
| 0.1 | 20 |
| 0 (TEP only, in absence of glutaraldehyde) | No activity |

These data clearly disclose that for the best results there must be employed an excess of glutaraldehyde over adsorbed TEP in order to prepare such an enzyme conjugate that retains an appreciable amount of activity after a relatively long period of operation.

EXAMPLE XIX

To illustrate the difference between a support matrix for immobilized enzymes which is prepared according to the process of the present invention with an immobilized enzyme concentrate in which the support matrix has been reduced with sodium borohydride to eliminate aldehyde functionality prior to adding the enzyme, a further series of immobilized enzyme conjugates were prepared. An alumina support which had an ABD of 0.82, a surface area of 14 m$^2$/gm, a pore distribution in which 88% was in a range of from 300 to 1500 Angstroms and a particle size of 20/40 mesh was treated with 4 ml of a 6.25% aqueous TEP solution per gram of support. After decanting and rinsing with water to remove excess TEP, treated support No. 1 was contacted with 3 ml of a 25% aqueous glutaraldehyde solution per gram of support, No. 2 with 1.5 ml of the glutaraldehyde solution, and No. 3 with 3 ml of the same solution. The No. 3 matrix, so prepared, was treated with aqueous sodium borohydride until all the free aldehyde functions were reduced. This was indicated by a negative color test with fuchsin-aldehyde reagent whereas prior to the borohydride treatment this test was positive indicating the presence of free aldehyde groups. Thereafter all of the matrices were treated with equal amounts of aqueous amyloglucosidase. The three immobilized enzyme conjugates were then packed into individual columns, 2 ml samples of each conjugate being used for each column. A commercially available, partially hydrolyzed starch solution (D.E.=15) was passed through the packed columns at a flow rate of 2.5 ml/minute for a period of 1 hour. At the end of the 1-hour period, the effluents were assayed for glucose to determine the activity of the conjugates. Following the determination of the activity, the conjugates were washed with an aqueous sodium chloride solution followed by a urea solution to facilitate desorption of physically adsorbed enzyme as contrasted with covalently bound enzyme. Hydrolyzed starch solution was again passed over the conjugates for an additional period of 1 hour. The effluents from each of the columns were then assayed and it was found that both of the conjugates which were prepared according to the process of the present application retained about 80% of their initial activity while the conjugate which had been reduced with sodium borohydride during its preparation in accordance with the Haynes et al teaching lost more than 50% of its original activity. Following this, the conjugates were further subjected to a continuous operation for a period of 20 hours, at the end of which time it was determined that the activity of conjugate No. 1 was 70% of the activity present at the start of the continuous operation while the activity of conjugate No. 3 was only 43% of the activity which was present at the beginning of the continuous operation. Accordingly, it follows that reduction of the free aldehyde moieties prior to binding the enzyme significantly decreases the stability of the conjugate.

EXAMPLE XX

As an illustration of the effect of pH when preparing the organic-inorganic support matrix to which an enzyme is covalently bound a further series of experiments were performed. Alumina spheres which possessed a surface area of 11 m$^2$/gm with a pore distribution in which 98% of the pores were in a range of from 500 to 1750 Angstroms were treated with aqueous TEP and glutaraldehyde according to the process of the present invention. The enzyme which was then bound to the polymeric-inorganic oxide support was amyloglucosidase. The inorganic oxide support had been treated with a 6% aqueous solution of TEP and a 12.5% solution of glutaraldehyde in each of three instances. In conjugates No. 1 and No. 2, the pH of the glutaraldehyde solution used in preparing the polymeric-inorganic oxide support was maintained at 7.0 while in conjugate No. 3 the pH was maintained at 3.5. A fourth conjugate was prepared in a manner similar to No. 1 but, prior to the addition of the enzyme, the polymeric-inorganic oxide support was reduced by the addition of sodium borohydride and tested for absence of free aldehyde groups with fuchsin-aldehyde reagent. As in the previous instances, the conjugates were used to treat a hydrolyzed starch solution in packed columns according to the following procedure. Initially the four conjugates were washed successively with aqueous sodium chloride and aqueous urea and then used to treat the hydrolyzed starch. After passage of the starch through the columns, for a period of 1 hour, the effluents were analyzed for glucose to determine the activity of the immobilized enzyme conjugates. The conjugates were then further washed with aqueous sodium chloride, aqueous urea and acidified urea and the treatment with starch again repeated. The results of these tests are set forth in Table VII below:

TABLE VII

| Conjugate | No. 1 | No. 2 | No. 3 | No. 4 |
|---|---|---|---|---|
| | After washing with aqueous sodium chloride and urea | | | |
| Units of activity/ gram of support | 1.7 | 1.9 | 1.5 | 1.3 |
| | After further washing with aqueous sodium chloride, urea, and acidified urea | | | |
| Units of activity/ gram of support | 1.7 | 1.7 | 1.4 | 1.0 |

It is noted from the above table that the two conjugates (No. 1 and No. 2) which were prepared according to the process of the instant application in which the formation of the polymer was accomplished while maintaining the glutaraldehyde at a pH of 7.0 showed relatively good activity after being subjected to a series of washes. In contradistinction to this, conjugate No. 4, which was prepared according to a process set forth in the prior art, i.e., by reduction with sodium borohydride prior to treatment with an enzyme while also maintaining the pH at 7.0, showed less activity after the first washings with aqueous sodium chloride and urea followed by a further loss of activity after being washed with additional amounts of aqueous sodium chloride, urea, and acidified urea. Again, it is demonstrated that elimination of aldehyde groups by borohydride reduction results in a less stable enzyme conjugate due to loss of covalent binding sites.

EXAMPLE XXI

To illustrate the effect which the addition of glutaraldehyde to the inorganic support which contains adsorbed TEP has on the activity of the finished immobilized enzyme conjugate an additional series of conjugates were prepared. Again the support comprised alumina particles which possessed a surface area of 11 m²/gm, a pore distribution in which 98% of the pores are in the range of from 500 to 1750 Angstroms and a particle size of about 30/40 mesh. The support was treated with a 6% solution of aqueous TEP and after decanting and rinsing with water, 20 cc of a 25% glutaraldehyde solution was added in four increments of 5 ml each time. After each addition, the contents were shaken and the liquid phase then decanted. One portion of the thus treated inorganic oxide support was formed into an immobilized enzyme conjugate by the addition of amyloglucosidase while the second portion was reduced with sodium borohydride prior to the addition of the enzyme. Again the two conjugates were used to treat a hydrolyzed starch solution in a manner similar to that set forth in the preceding paragraph, the activity of the conjugate being determined by assaying the effluent for glucose. The results of these tests after washing successively with sodium chloride and urea solutions of varying pH are set forth in Table VIII below in which conjugate No. 1 is the conjugate prepared according to the process of the present application and conjugate No. 2 is the conjugate prepared according to the process set forth in the cited art.

TABLE VIII

|  | Activity (Units/Gram of Support) | |
| --- | --- | --- |
|  | No. 1 | No. 2 |
| Initial Activity | 2.4 | 2.0 |
| After NaCl & urea washes (8.5 pH) | 2.3 | 1.5 |
| After 4-day rest at room temp. | | |
| Initial Activity | 2.0 | 1.2 |
| After NaCl Wash | 2.0 | 1.1 |
| After pH 4.2, Urea Wash | 2.0 | 1.0 |
| After pH 4.0, NaCl Wash | 1.9 | 0.9 |
| After pH 8.7, NaCl Wash | 1.8 | 0.8 |
| After pH 3.3, Urea Wash | 0.5 | 0.2 |

It is readily apparent from a comparison of the two conjugates that in addition to possessing a higher initial activity the conjugate of the present invention maintains its activity at a relatively high level over a much longer set of washings at various pH conditions than did the conjugate prepared according to the cited reference. The relatively large drop in activity of both conjugates at pH 3.3 can undoubtedly be attributed to the well-known deactivating affect of such acidic conditions on amyloglucosidase.

EXAMPLE XXII

In the following set of experiments, the alumina support which was utilized to prepare immobilized enzyme conjugates according to the above paragraph was treated with a 5% aqueous solution of polyethyleneimine (mol. wt.=1800-Dow Chemical Co.) ("PEI-18"). Again the alumina which was treated with the aforementioned polyethyleneimine solution was further treated with glutaraldehyde and then with amyloglucosidase according to the process of the present invention to form conjugate No. 1. Conjugate No. 2 was formed with an intermediate borohydride reduction, but without the final step of cross-linking with glutaraldehyde following the addition of the enzyme. Conjugate No. 3 was also formed in a manner similar to that used to prepare conjugate No. 2, but with the final cross-linking effected by the further addition of glutaraldehyde. Conjugates No. 4 and No. 5 were prepared in similar fashion but omitted any removal or decantation of unadsorbed "PEI-18", conjugate No. 4 being without the final cross-linking and conjugate No. 5 with the final cross-linkage. The conjugates were then used to treat a hydrolyzed starch solution as previously described. After treatment of the starch solution followed by activity determinations, the five conjugates were washed, the first wash being with distilled water followed by an acetate buffer at pH=4.2, the second wash with a 2 molar sodium chloride solution, and wash No. 3 with a sodium chloride plus ethylene glycol solution, while wash No. 4 was again with a 2 molar sodium chloride solution. As in the preceding experiments, after each wash the conjugates were used to treat hydrolyzed starch and the activity determined after a 1 hour period. The results of these experiments are set forth in Table IX below.

TABLE IX

|  | 1 | 2 | 3 | 4 | 5 |
| --- | --- | --- | --- | --- | --- |
| Initial Activity (Units/gram) | 2.5 | 1.8 | 1.1 | 2.9 | 1.9 |
| A — Wash No. 1 | 2.5 | 1.6 | 1.0 | 2.7 | 1.9 |
| B — Wash No. 2 | 2.4 | 1.2 | 1.0 | 1.9 | 1.9 |
| C — Wash No. 3 | 2.3 | 1.1 | 0.9 | 1.8 | 1.8 |
| D — Wash No. 4 | 2.2 | 1.0 | 0.9 | 1.6 | 1.6 |

The results set forth in this table indicate that the conjugate which was prepared according to the process of the instant application possessed a relatively high initial activity which was retained to a large extent even after repeated washings with the various solutions indicated. In contradistinction to this, the conjugates which were prepared using known methods, employing reduction using sodium borohydride, showed that these conjugates lost either a relatively large amount of their activity after the repeated washings (Nos. 2 and 4) or, if they retained a relatively greater percent activity as in Nos. 3 and 5, in which a final cross-linking was used, the level of activity was less than the activity of the immobilized enzyme conjugate of the present application (No. 1).

EXAMPLE XXIII

To illustrate the necessity for utilizing an inorganic porous support which possesses the physical characteristics hereinbefore set forth, that is, the requisite pore diameters, surface areas, etc., a series of experiments were conducted in which a support matrix for immobilizing enzymes was prepared according to the process of the present invention. In addition, a different support matrix utilizing colloidal silica as the inorganic support which was treated with polyethyleneimine and glutaraldehyde according to the prior art was also prepared. In accordance with the prior art a 2.5% aqueous glutaraldehyde solution was slowly added with vigorous stirring to provide a stirrable suspension of the conjugate followed by adding a 25% aqueous solution of glutaraldehyde to the polyethyleneimine treated colloidal silica suspension. The result of this addition was an agglomeration of the silica and so-formed polymer to produce an intractable mass. The same result also occurred when the polyethyleneimine treated colloidal silica was first centrifuged away from unadsorbed polyethyleneimine and then added to the 25% aqueous glutaraldehyde solution. It was therefore readily apparent that a support matrix to which an enzyme could be covalently bound could not be prepared when utilizing particles of colloidal dimension.

We claim as our invention:

1. A process for the preparation of a support matrix for immobilization of enzymes which comprises treating an inorganic porous support material selected from the group consisting of gamma-alumina, silica, zirconia, silica-magnesia, silica-zirconia-alumina, and silica-alumina, said material possessing pore diameters of from about 100 to about 55,000 Angstroms and a surface area of from about 1 to about 500 square meters per gram, with a solution of water soluble polyamines selected from the group consisting of ethylenediamine, diethylenetriamine, triethylenetetramine, tetraethylenepentamine, pentaethylenehexamine, hexamethylenediamine, and polyethyleneimine, removing unabsorbed polyamines after said treatment, contacting the treated support material with a solution containing a molar excess of a bifunctional monomeric material selected from the group consisting of glutaraldehyde and toluenediisocyanate, wherein said bifunctional monomer reacts with said polyamine material absorbed on said support, removing unreacted bifunctional monomeric material solution, and recovering the resultant inorganic-organic support matrix.

2. The process as set forth in claim 1 in which said treatment is effected at a temperature in the range of from about 5° to 60° C.

3. The process as set forth in claim 1 in which said bifunctional monomeric material is present in an excess of from about 3 to about 50 or more moles of said bifunctional monomer per mole of said water soluble polyamine.

4. The process as set forth in claim 1 in which said support is gamma-alumina.

5. The process as set forth in claim 1 in which said silica-alumina material contains boron phosphate.

6. The process as set forth in claim 1 in which said bifunctional monomer is glutaraldehyde.

7. The process as set forth in claim 1 in which said bifunctional monomer is toluenediisocyanate.

8. A support matrix prepared by the process steps of claim 1.

9. The support matrix as set forth in claim 8 in which said support is gamma-alumina.

10. The support matrix prepared by the process steps of claim 1 in which said water soluble polyamine is polyethyleneimine.

11. The support matrix prepared by the process steps of claim 1 in which said water soluble polyamine is tetraethylenepentamine.

12. The support matrix prepared by the process steps of claim 1 in which said bifunctional monomer is glutaraldehyde.

13. The support matrix prepared by the process steps of claim 1 in which said bifunctional monomer is toluenediisocyanate.

14. The support matrix as prepared by the process steps of claim 1 wherein the polymeric portion of said matrix is effected in situ on said alumina material.

* * * * *